United States Patent

McGrath

(10) Patent No.: US 8,740,782 B2
(45) Date of Patent: Jun. 3, 2014

(54) LARYNGOSCOPE

(75) Inventor: Matthew J. R. McGrath, Aviemore (GB)

(73) Assignee: Aircraft Medical Ltd., Edinburgh (GB)

(*) Notice: Subject to any disclaimer, the term of this patent is extended or adjusted under 35 U.S.C. 154(b) by 78 days.

(21) Appl. No.: 10/451,421

(22) PCT Filed: Dec. 21, 2001

(86) PCT No.: PCT/GB01/05611
§ 371 (c)(1),
(2), (4) Date: Jan. 13, 2004

(87) PCT Pub. No.: WO02/051304
PCT Pub. Date: Jul. 4, 2002

(65) Prior Publication Data
US 2004/0127770 A1 Jul. 1, 2004

(30) Foreign Application Priority Data
Dec. 23, 2000 (GB) .................................. 0031621.6

(51) Int. Cl.
*A61B 1/267* (2006.01)
(52) U.S. Cl.
USPC ........... 600/196; 600/185; 600/188; 600/190; 600/193; 600/197
(58) Field of Classification Search
USPC ......... 600/185, 188, 190, 193, 196, 197, 235, 600/237, 238
See application file for complete search history.

(56) References Cited

U.S. PATENT DOCUMENTS

| | | | | |
|---|---|---|---|---|
| 1,908,010 | A * | 5/1933 | Cameron | 600/241 |
| 2,649,087 | A * | 8/1953 | Allyn et al. | 600/193 |
| 3,900,924 | A * | 8/1975 | Meltzner | 600/241 |
| 4,213,451 | A * | 7/1980 | Swenson | 600/215 |
| 4,273,112 | A | 6/1981 | Heine et al. | |
| 4,384,570 | A | 5/1983 | Roberts | 128/4 |
| 4,425,909 | A * | 1/1984 | Rieser | 600/197 |
| 4,437,458 | A * | 3/1984 | Upsher | 600/193 |
| 4,546,762 | A * | 10/1985 | Upsher | 600/193 |
| 4,556,052 | A * | 12/1985 | Muller | 600/193 |
| 4,574,784 | A * | 3/1986 | Soloway | 600/193 |
| 4,669,449 | A | 6/1987 | Bauman | 128/11 |
| 4,947,829 | A * | 8/1990 | Bullard | 600/101 |
| 5,003,963 | A * | 4/1991 | Bullard et al. | 600/104 |
| 5,036,835 | A | 8/1991 | Filli | 128/11 |
| 5,060,633 | A * | 10/1991 | Gibson | 600/193 |
| 5,092,314 | A * | 3/1992 | Zeitels | 600/194 |
| 5,184,603 | A * | 2/1993 | Stone | 600/193 |
| 5,263,472 | A * | 11/1993 | Ough | 600/188 |

(Continued)

FOREIGN PATENT DOCUMENTS

GB 2191949 A 12/1987

OTHER PUBLICATIONS

RSA Annual Report 2000.
Extract from RSA Student Design Award 1999/2000 CD-ROM.

(Continued)

*Primary Examiner* — Matthew J Kasztejna
(74) *Attorney, Agent, or Firm* — Nixon & Vanderhye P.C.

(57) ABSTRACT

The invention relates to a laryngoscope (1) that has been adapted to improve comfort during use. The important adaptations are that the laryngoscope handle (4) is offset and in one embodiment the handle (4) is pivotably connected to a receiving portion (5).

22 Claims, 7 Drawing Sheets

(56) References Cited

U.S. PATENT DOCUMENTS

| | | | |
|---|---|---|---|
| 5,287,848 A * | 2/1994 | Cubb et al. | 128/200.26 |
| 5,381,787 A * | 1/1995 | Bullard | 600/188 |
| 5,651,760 A | 7/1997 | Upsher | 600/193 |
| 5,800,342 A * | 9/1998 | Lee et al. | 600/114 |
| 5,800,344 A * | 9/1998 | Wood et al. | 600/188 |
| 5,827,178 A * | 10/1998 | Berall | 600/188 |
| 6,077,286 A | 6/2000 | Cuschieri et al. | |
| 6,095,972 A * | 8/2000 | Sakamoto | 600/190 |
| 6,123,666 A * | 9/2000 | Wrenn et al. | 600/188 |
| 6,217,512 B1 * | 4/2001 | Salo et al. | 600/160 |
| 6,354,993 B1 * | 3/2002 | Kaplan et al. | 600/188 |
| 6,520,909 B1 * | 2/2003 | Rankins | 600/196 |
| 6,764,443 B1 * | 7/2004 | Watson | 600/197 |

OTHER PUBLICATIONS

Letter from British Library dated Nov. 29, 2007.
Email from Janet Hawken to Joseph Lenthall dated Nov. 28, 2007.
Opposition Grounds in May 6, 2009 Letter from Mewburn Ellis LLP.

* cited by examiner

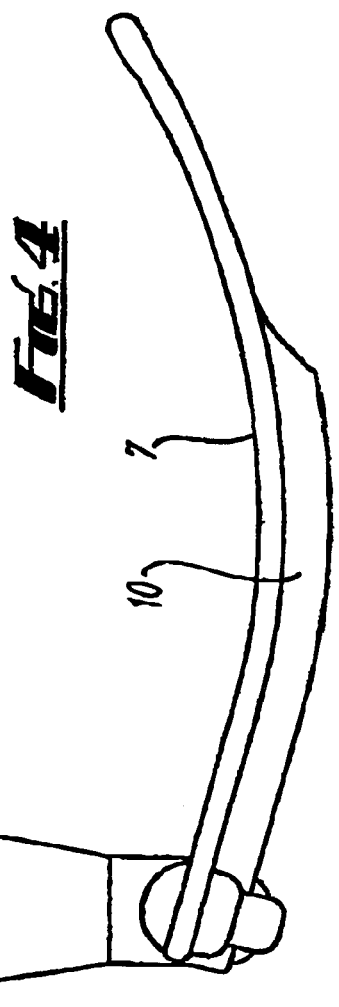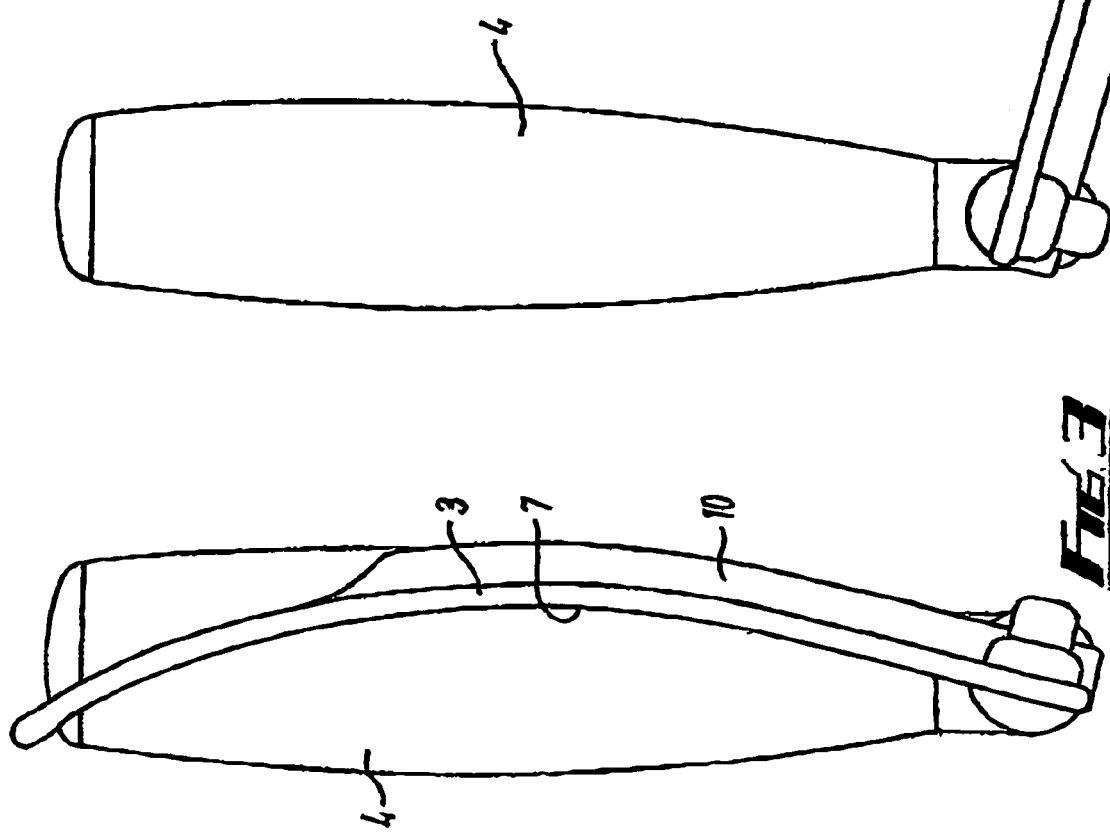

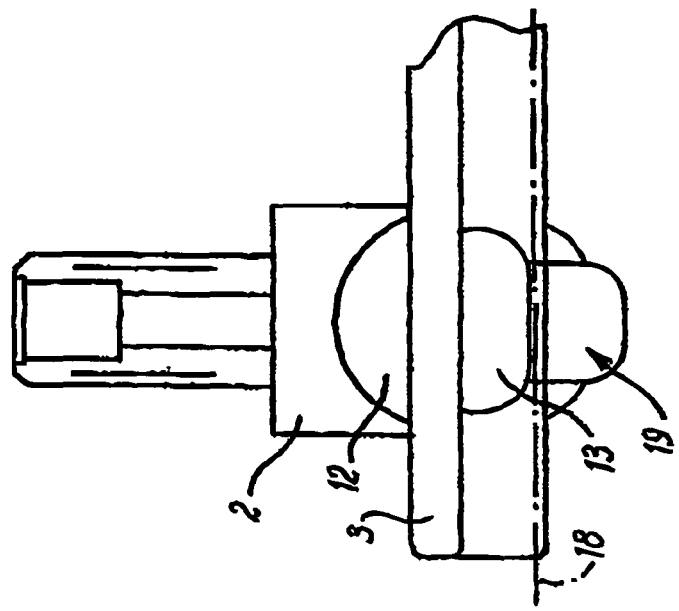
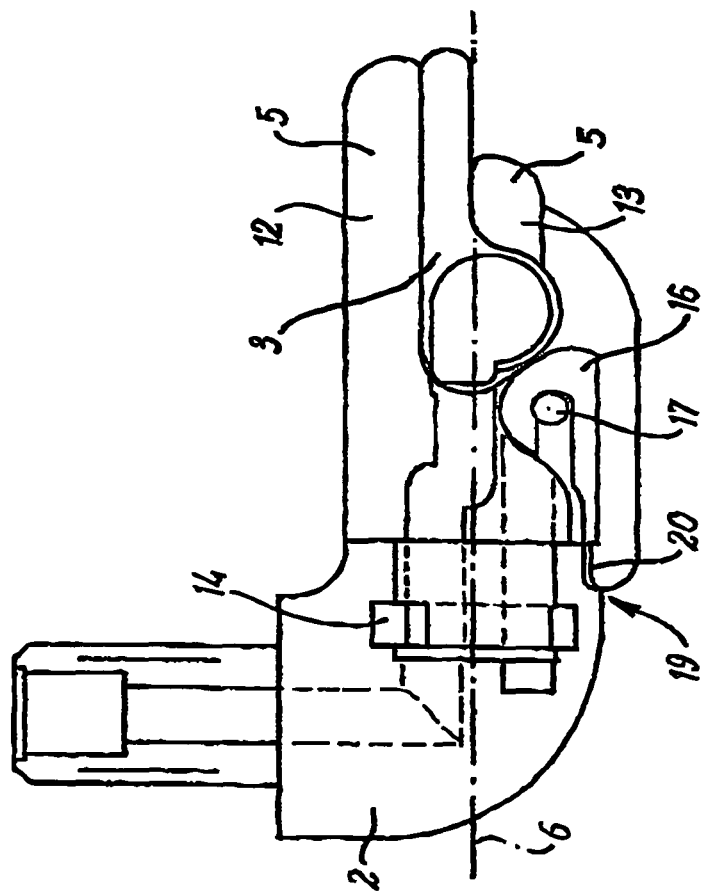

LARYNGOSCOPE

BACKGROUND OF THE INVENTION

The present invention relates to laryngoscopes and relates particularly to laryngoscopes to assist intubation of a tracheal tube.

Insertion of a tracheal tube is an important procedure in providing an airway to an anaesthetist prior to a surgical operation. Tracheal tubes also often need to be inserted in an emergency situation into the airway of an unconscious patient by paramedics or doctors. Insertion of a tracheal tube requires significant skill, and laryngoscopes are generally used to assist the insertion of the tube by restraining the patient's tongue and allowing a clear view of the larynx and the entrance to the trachea. Considerable skill and care is required in carrying out this procedure in order to avoid damage to the patient's teeth and soft tissue of the throat.

A known laryngoscope is disclosed in U.S. Pat. No. 5,036,835. This known laryngoscope comprises an elongate blade for insertion into the patient's mouth and which is attached in use to a handle extending generally at right angles to the blade such that the blade and handle lie generally in the same plane.

Most, if not all, prior art laryngoscopes are of the type described above in which the blade and handle lie generally in the same plane. These known laryngoscopes suffer from the drawback that because the blade and handle occupy the same plane, the user's hand obscures the view into the patient's throat, making the laryngoscope more difficult to use In addition, known laryngoscopes are usually stored in a folded condition in which the handle extends generally parallel to the blade. This frequently results in the drawback that blood and other body fluids on the blade come into contact with the handle, causing a risk of cross contamination when the handle subsequently comes into contact with the sterilised blade, thus potentially transferring infection between patients. In addition to the above disadvantages, prior art laryngoscopes often require a series of blades of different sizes to accommodate different sizes of patient.

SUMMARY OF THE INVENTION

Preferred embodiments of the present invention seek to overcome the above disadvantages of the prior art.

According to a first aspect of the present invention, there is provided a laryngoscope comprising a body portion having a receiving portion for receiving an elongate blade adapted to be inserted into a patient's mouth, and a handle pivotably connected to said receiving portion about an axis and spaced apart from said receiving portion in the direction of said axis, wherein when a blade is received in said receiving portion, the handle is pivotable about said axis between a fold condition in which the handle extends substantially parallel to the blade, and a working condition in which the handle extends substantially transversely to said blade.

By providing a handle which is spaced in use from the blade in the direction of the pivot axis, this provides the simultaneous advantages of providing a less obstructed view into the mouth of the patient when in use, thus making the laryngoscope easier to use, while also avoiding contact between the blade and the handle when in the folded condition, thus minimising the risk of cross contamination when the laryngoscope is in the folded condition.

In a preferred embodiment, the position of at least one said blade in use relative to the receiving portion is adjustable in at least one orientation of the handle relative to the blade between said working and folded conditions.

This provides the advantage that the effective length of the blade in use can be adjusted so that a set of separate blades of different lengths is not required.

The blade in use is preferably gripped by said receiving portion in said working condition.

The receiving portion preferably further comprises cam means and a set of jaws for gripping a said blade, wherein movement of said handle about said axis from said working condition to at least one orientation between said working and folded conditions moves said jaws further apart.

This provides the advantage that in moving the handle to the working condition, the jaws automatically grip the blade to hold it in position, while automatically releasing the blade as the handle is moved to the orientation between the working and folded conditions.

The blade may be gripped by said receiving portion in said folded condition.

By also gripping the blade in the folded condition, this provides the advantage that movement of the blade in the folded condition is minimised, thus minimising the risk of the blade coming into contact with contamination.

In a preferred embodiment, movement of said handle from said at least one orientation into said folded condition moves said jaws closer together.

The laryngoscope preferably further comprises at least one said blade.

According to a second aspect of the present invention, there is provided a laryngoscope comprising a body portion having a receiving portion for receiving an elongate blade adapted to be inserted into a patient's mouth, and a handle connected to said receiving portion, wherein said receiving portion grips said blade in such a manner that the blade is spaced apart from said handle.

Preferably the receiving portion is able to receive the blade at a number of different points along the length of the blade.

Preferably the receiving portion comprises a cam means and a set of jaws for gripping said blade.

Optionally the laryngoscope (according to either aspect of the invention) further comprises an image gathering facility.

A further option is that the laryngoscope also comprises an image viewing means.

The laryngoscope preferably further comprises illumination means including a light source located in at least one said blade.

In a preferred embodiment, the light source is located remotely from the distal end of said blade, and the laryngoscope further comprises light guide means for directing light from said light source to a location adjacent to the distal end of the blade.

By separating the light source from the distal end of the blade by means of light guide means, this provides the advantage of minimising the risk of the patient being burned by the light source.

The laryngoscope may further comprise a power supply provided in the body portion for supplying electrical power to said light source.

The laryngoscope preferably further comprises a plurality of electrical terminals provided on at least one said blade for connecting said light source to said power supply.

Preferably the laryngoscope further comprises a camera facility in at least one blade.

Most preferably the laryngoscope also comprises a viewing screen.

The handle may have a coating of elastomeric and/or polymeric material.

In the case of an elastomeric material such as rubber, this provides the advantage of facilitating cleaning of the handle, thus minimising the risk of dirt being harboured in the handle.

BRIEF DESCRIPTION OF THE DRAWINGS

A preferred embodiment of the invention will now be described, by way of example only and not in any limitative sense, with reference to the accompanying drawings, in which:

FIG. 3 is a side elevation view of the laryngoscope of FIG. 1 in a folded condition;

FIG. 4 is a side elevation view of the laryngoscope of FIG. 2 in an unfolded condition;

FIG. 8 is a rear view of the laryngoscope of FIG. 2 with the handle removed;

FIG. 9 is a side view of the part shown in FIG. 8;

DETAILED DESCRIPTION OF PERFERRED EMBODIMENTS

Figure 1:
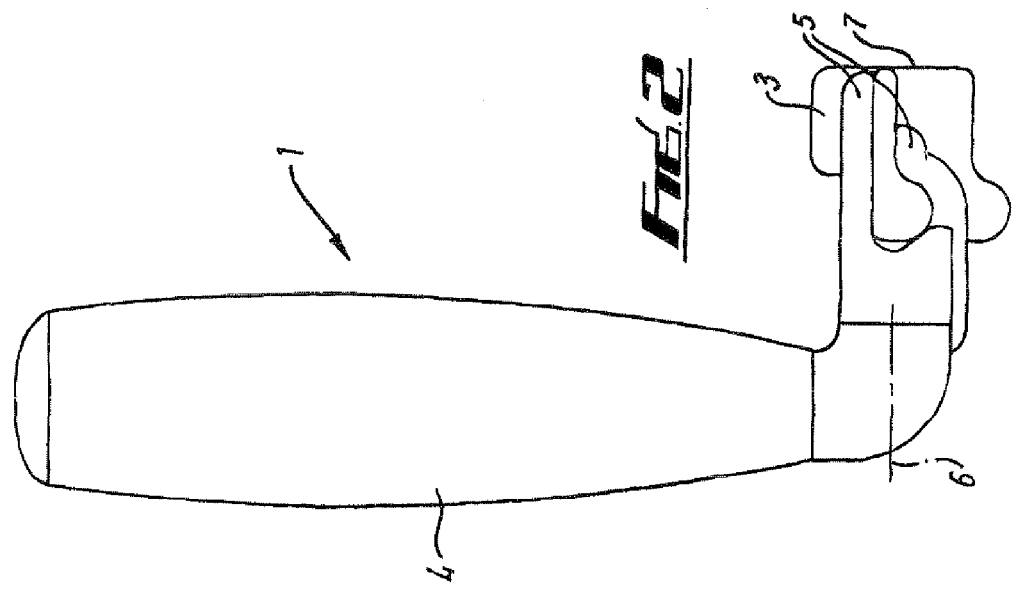
FIG. 1 is a rear view of a laryngoscope embodying the first aspect of the present invention in a folded condition thereof.
Figure 2:
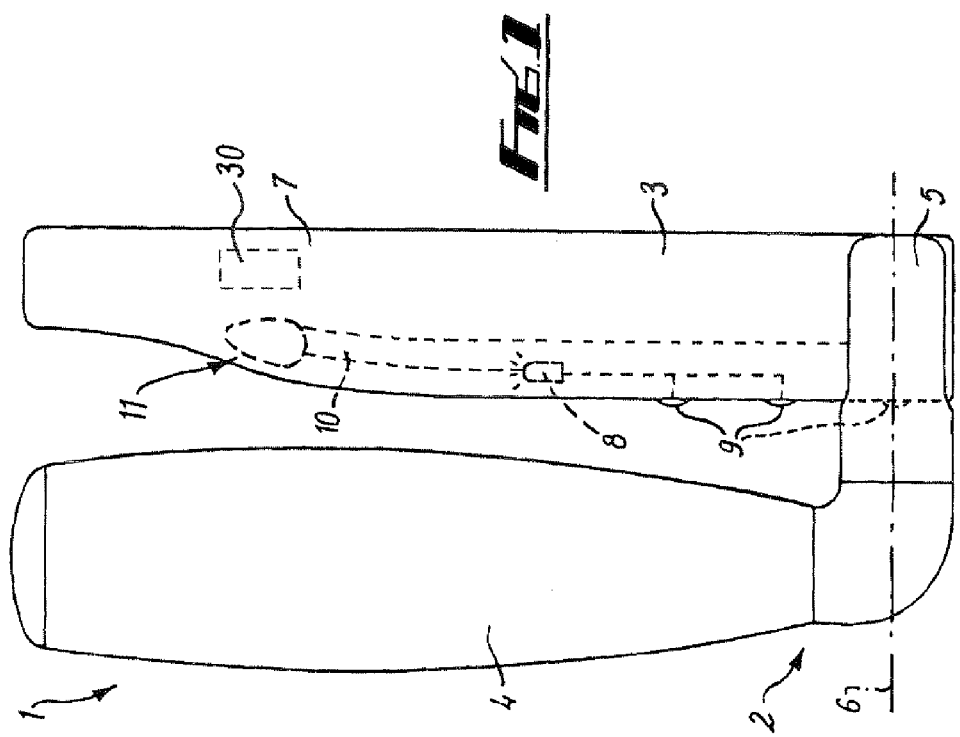
FIG. 2 is a rear view of the laryngoscope of FIG. 1 in an unfolded condition.

Referring to FIGS. 1 to 4, a laryngoscope 1 has a body portion 2 and a blade 3. The body portion 2 includes a handle 4 having a coating of rubber or similar elastomeric and/or polymeric material to enable the handle 4 to be gripped by a user and to be cleaned, and a pair of jaws 5 for receiving the blade 3. The jaws 5 are pivotable about axis 6 relative to the handle 4 between a working condition (as shown in FIG. 2) in which the handle 4 extends generally at right angles to the blade 3 and a folded condition (shown in FIG. 1) in which the handle 4 extends generally parallel to the blade 3. A cam mechanism (not shown) provided on the body portion 2 adjusts the separation of the jaws 5 such that the jaws 5 are further apart when the blade received between the jaws 5 is at an orientation between the working and folded conditions than they are when the handle 4 is in the working or folded condition. The operation of the cam mechanism will be described in greater detail below.

The blade 3 has an elongate curved surface 7 for restraining the tongue of a patient and providing visual access to the opening of the trachea, and a light source comprising a bulb 8 connected to a series of electrical pick-ups 9 on the edge of the blade 3 and connected via a fibre optic tube 10 to a light outlet 11 near the distal end of the blade 3. The blade 3 is adjustably received between jaws 5 such that an electrical pick-up 9 can be aligned with a corresponding electrical terminal (not shown) on the body portion 2 which is in turn connected to a power supply 32 such as a battery located in the handle 4. This enables the light source to illuminate a patient's throat, but the separation of the bulb 8 and outlet 11 avoids burning of the patient's throat by the bulb 8.

Referring now to FIGS. 8 to 12, the jaws 5 comprise an upper clamp arm 12 and a moveable lever 13, the blade 3 being clamped between the underside of the clamp arm 12 and the upper surface of the lever 13. The clamp arm 12 and lever 13 are pivotably attached to the body portion 2 by means of an interlocking key mechanism 14 having a key surface 15 (FIGS. 10 to 12) such that the jaws 5 can rotate about axis 6 through a maximum of 90 degrees, i.e., between the working and folded conditions.

The lever 13 and clamp arm 12 are attached to each other by means of a hook 16 and bar 17, so that the lever 13 can pivot about axis 18 (FIGS. 10 to 12) relative to clamp arm 12. The end 19 of the lever 13 facing the body portion 2 co-operates with a cam surface 20 on the underside of the body portion 2, such that as the handle is rotated relative to the jaws 5, the separation between the end 19 of the lever 13 and the corresponding surface of the clamp arm 12 varies. In particular, the cam surface 20 is so shaped that when the handle 4 is in the working and folded conditions, the separation between the end 19 of the lever 13 and the corresponding surface of the clamp arm 12 is a maximum, thus causing the jaws 5 to grip the blade 3, while at orientations between the working and folded conditions, the separation between the jaws 5 is sufficient that the position of the blade 3 can be adjusted relative to the body portion 2.

The operation of the laryngoscope 1 will now be described with reference to FIGS. 5 to 7.

Figure 5:
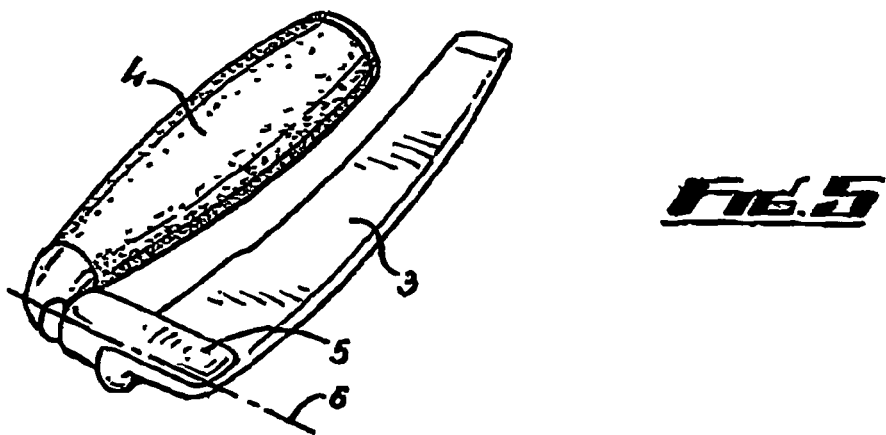
FIGS. 5 to 7 illustrate the process of setting the effective length of blade of the laryngoscope of FIGS. 1 to 4 and maintaining the blade in position.

In its storage (i.e., folded) condition, as shown in FIG. 5, the blade 3 extends generally parallel to the handle 4, but is displaced from the handle in the direction of pivot axis 6. While the laryngoscope is in its folded condition, the blade 3 and handle 4 axe sufficiently far apart in the direction of the axis 6 to avoid contact between the handle and the blade. As described above with reference to FIGS. 8 to 12, in the folded condition, the jaws 5 are urged towards each other to grip to blade 3.

Figure 6:
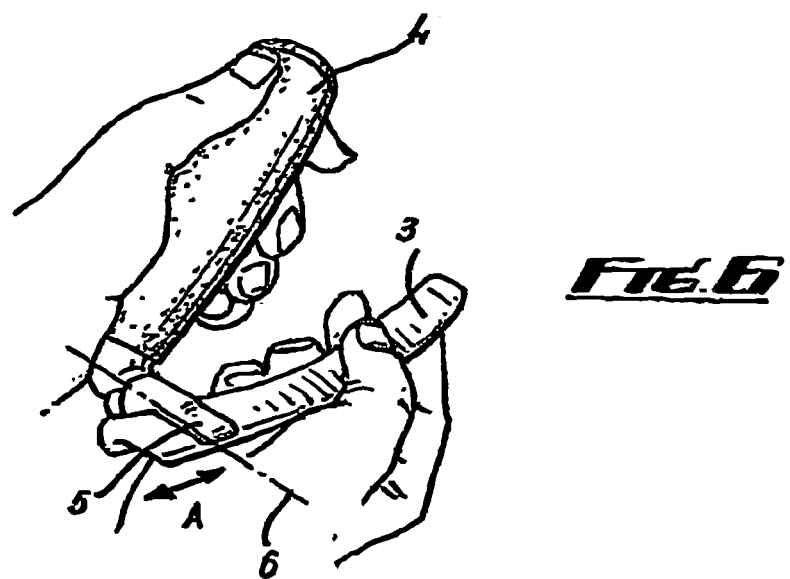

Referring now to FIG. 6, as the handle 4 is rotated about axis 6 relative to the blade 3 in the direction of the working condition, the cam surface 20 engaging the end 19 of lever 13 enables the jaws 5 to move sufficiently far apart that the blade 3 can slide in the direction of arrow A in FIG. 6 between the jaws 5. In this way, the blade length is selected such that one of the electrical pick-ups 9 is placed in contact aligned with the electrical terminal provided on the body portion 2 to connect the light source to the power supply in the handle 4, while a length of blade 3 suitable for the size of patient protrudes from the jaws S.

Figure 7:
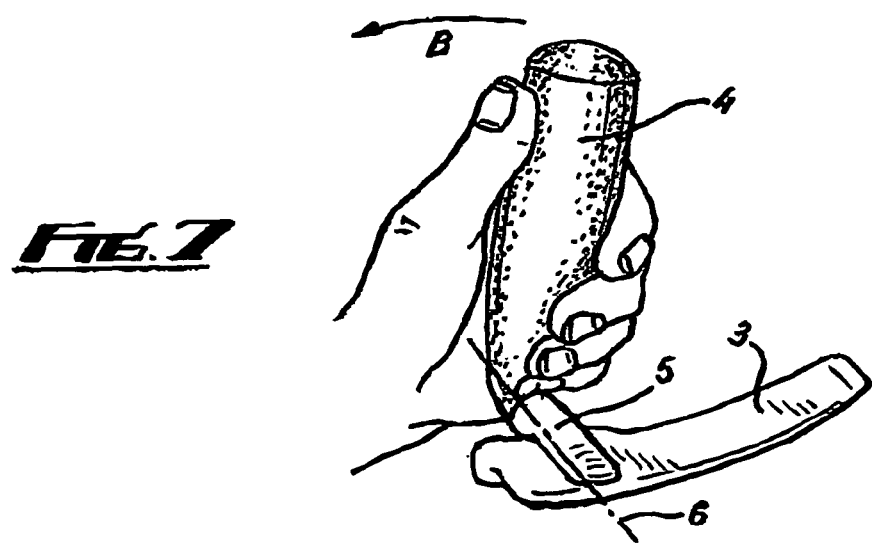
Figure 10:
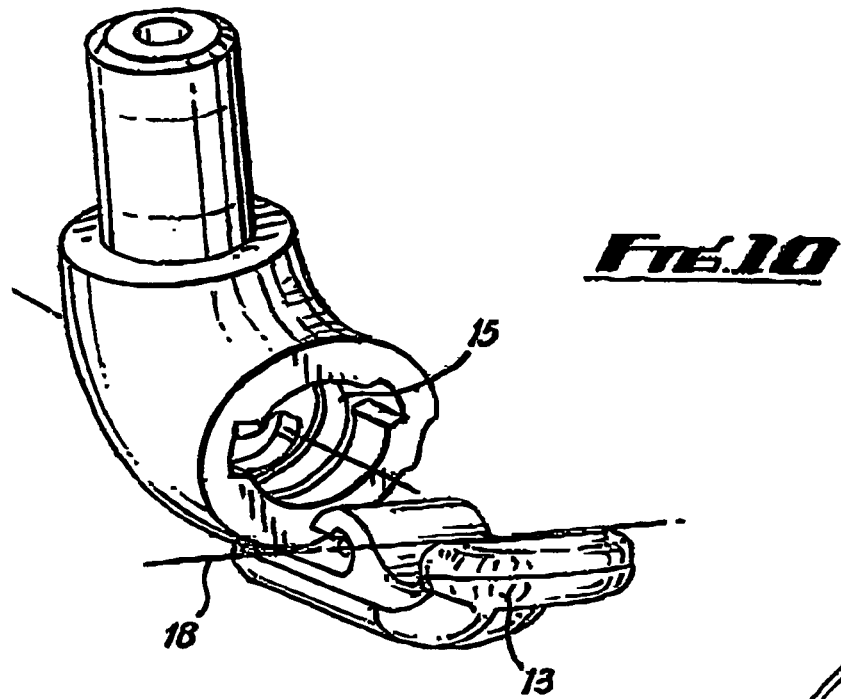
FIGS. 10 to 12 show the cam surfaces of the body portion of the laryngoscope of FIGS. 8 and 9 in moving from the working to the folded condition.
Figure 11:
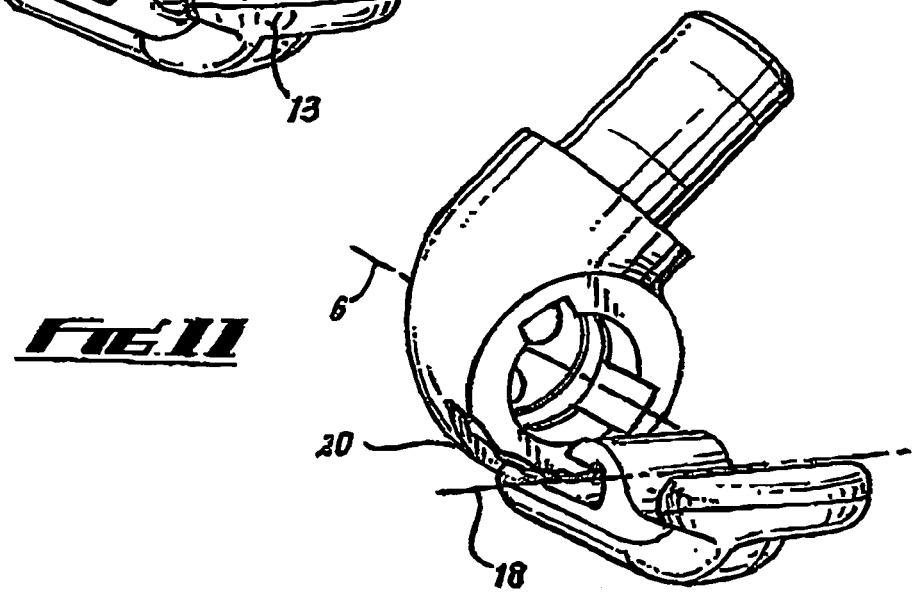
Figure 12:
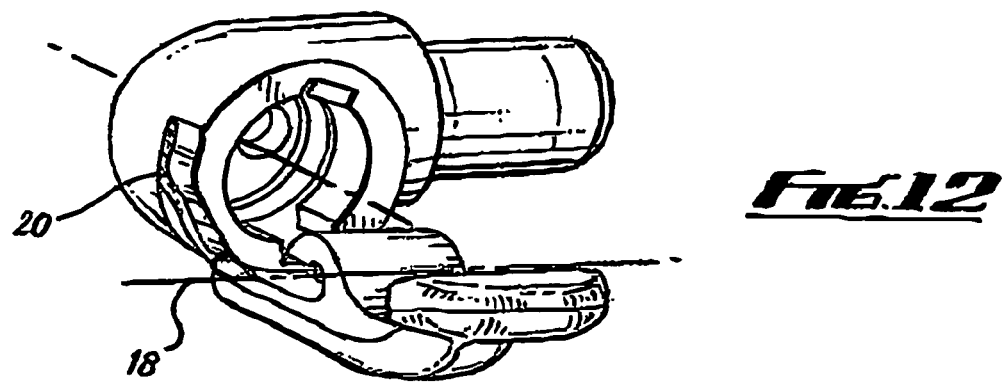

When the desired working length of blade 3 protrudes from jaws 5, then handle 4 is then rotated in the direction of arrow B shown in FIG. 7 about axis 6 until the handle 4 is generally at right angles to the blade 3. As the handle rotates about axis 6, the cam surface 20 causes the jaws 5 to move closer together to hold the blade 3 in the set position. The blade 3 is then held in position, but because the handle 4 is displaced from the blade 3 in the direction of axis 6 as shown in FIG. 7, an unobstructed view into the patient's throat is provided.

Figure 13:
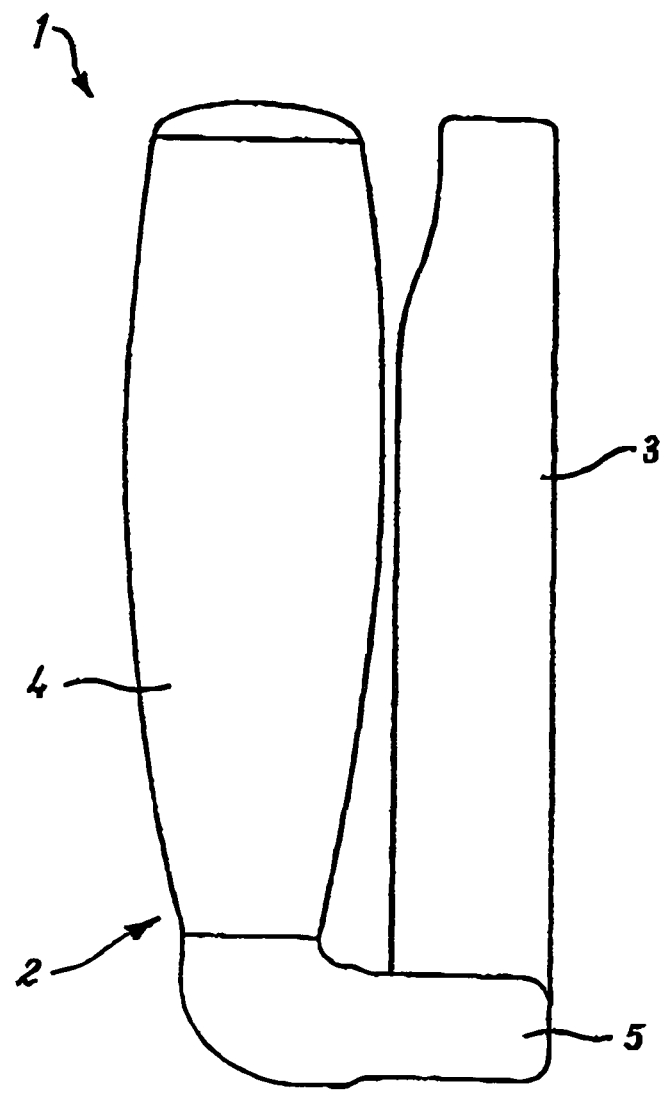
FIG. 13 shows a laryngoscope according to the second aspect of the present invention.
Figure 14:
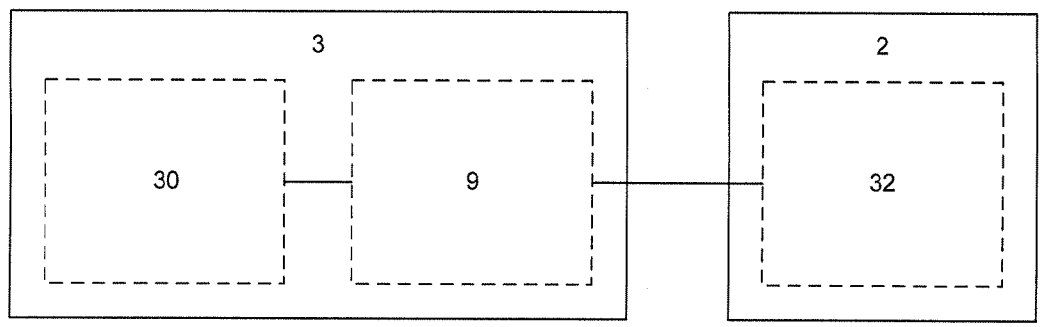
FIG. 14 is a schematic diagram showing an embodiment of a laryngoscope in which a plurality of electrical terminals is provided on a blade and configured to connect image gathering means to a power supply
Figure 15:
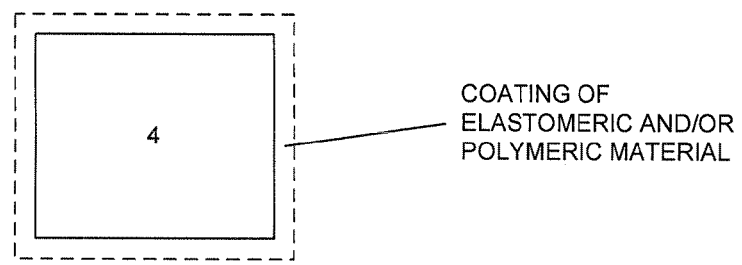
FIG. 15 is a schematic diagram showing an embodiment of a laryngoscope with a handle that has a coating of elastomeric and/or polymeric material.
Figure 16:
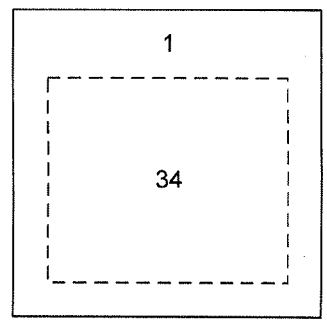
FIG. 16 is a schematic diagram showing an embodiment of a laryngoscope having a viewing device attached that is configured to display an image.

According to a second embodiment (as shown in FIG. 13) a laryngoscope 1 is provided that has a body portion 2 and blade 3. In this embodiment the body portion 2 comprises a receiving jaw portion 5 which is only slightly offset from the handle 4. The slight offset means that the laryngoscope is comfortable in use.

In either embodiment, the laryngoscope 1 may be provided with an image gathering facility 30 and viewing means 34. The viewing means may be attached to the laryngoscope 1, wired to the laryngoscope or completely separate from the laryngoscope.

It will be appreciated by persons skilled in the art that the above embodiment has been described by way of example only, and not in any limitative sense, and that various alterations and modifications are possible without departure from the scope of the invention as defined by the appended claims. For example, the laryngoscope may be designed so that the blade is not gripped in the folded condition.

The invention claimed is:

1. A laryngoscope, comprising:
    a handle, wherein the handle has a coating of elastomeric and/or polymeric material;
    a blade configured to be inserted into a patient's mouth;
    a camera located within the blade;
    a light source located in the blade, wherein the light source is located remotely from the distal end of said blade;
    a light guide that directs light from said light source to a location adjacent to the distal end of the blade;
    a viewing device attached to the laryngoscope and configured to display an image;
    a plurality of electrical terminals provided on said blade and configured to connect said light source and camera to a power supply; and
    a mounting portion attacked to an end of the handle and configured to adjustably couple the blade to the handle so that a working length of the blade may be adjusted, wherein a central longitudinal axis of the handle is located in a first plane, wherein a central longitudinal axis of the blade is located in a second plane, the first and second planes being offset with respect to one another in a direction that is perpendicular to both planes, wherein when the blade is in a working condition, the blade does not extend in a direction parallel to the handle along the entire length of the blade, wherein the mounting portion is configured to adjust a working length of the blade relative to the handle when the laryngoscope is in the working condition, and wherein the mounting portion is configured such that a proximal portion of the blade extends rearward beyond the central longitudinal axis of the handle when a working length of the blade is less than a predetermined lenghth and the laryngoscope is in a working condition.

2. The laryngoscope as described in claim 1, wherein one of the handle and the blade are pivotably connected to the mounting portion, such that a longitudinal axis of the handle extends substantially parallel to a longitudinal axis of the blade when the laryngoscope is in a folded condition.

3. The laryngoscope according to claim 2, wherein the position of the blade in use relative to the mounting portion is adjustable in at least one orientation of the handle relative to the blade between said working and folded conditions.

4. The laryngoscope according to claim 2, wherein the blade in use is gripped by said mounting portion.

5. The laryngoscope according to claim 2, wherein the mounting portion further comprises a set of jaws configured to hold said blade in position.

6. The laryngoscope according to claim 5, wherein the mounting portion further comprises cam means, wherein movement of said handle relative to said blade from said working condition to at least one orientation between said working and folded conditions moves said jaws further apart.

7. The laryngoscope according to claim 6, wherein movement of said handle relative to said blade from said at least one orientation into said folded condition moves said jaws closer together.

8. The laryngoscope according to claim 2, wherein the blade is gripped by said mounting portion in said folded condition.

9. The laryngoscope according to claim 5, wherein the jaws are configured to hold a proximal end of the blade within the jaws when the blade is at a fully extended working length, and wherein the proximal end of the blade extends outward from a rear portion of the jaws when a working length of the blade is less than a predetermined length.

10. The laryngoscope according to claim 1, further comprising a power supply located in the handle and configured to supply electrical power to said light source, camera and viewing device.

11. The laryngoscope according to claim 1, wherein the handle is in an upright position when the laryngoscope is in the working condition.

12. The laryngoscope of claim 1,
    wherein when the blade is in the working condition, a top surface of a portion of the blade coupled to the mounting portion is positioned at an oblique angle with respect to the central longitudinal axis of the handle.

13. The laryngoscope of claim 1, further comprising a receiving portion on the handle for receiving the blade, the receiving portion being pivotable about an axis.

14. The laryngoscope of claim 13, wherein the receiving portion is rotatable between a working position and a folded position.

15. A laryngoscope, comprising:
    a handle, wherein the handle has a coating of elastomeric and/or polymeric material;
    a blade configured to be inserted into a patient's mouth;
    a camera located within the blade;
    a light source located in the blade, wherein the light source is located remotely from the distal end of said blade;
    a light guide that directs light from said light source to a location adjacent to the distal end of the blade;
    a viewing device attached to the laryngoscope and configured to display an image;
    a plurality of electrical terminals provided on said blade and configured to connect said light source and camera to a power supply;
    a mounting portion attached to an end of the handle and configured to adjustably couple the blade to the handle so that a working length of the blade may be adjusted, wherein a central longitudinal axis of the handle is located in a first plane, wherein a central longitudinal axis of the blade is located in a second plane, the first and second planes being offset with respect to one another in a direction that is perpendicular to both planes, wherein when the blade is in a working condition, the blade does not extend in a direction parallel to the handle along the entire length of the blade, wherein one of the handle and the blade are pivotably connected to the mounting portion, such that a longitudinal axis of the handle extends substantially parallel to a longitudinal axis of the blade when the laryngoscope is in a folded condition, and wherein the mounting portion further comprises a set of jaws configured to hold said blade in position.

16. The laryngoscope according to claim 15, wherein the mounting portion further comprises cam means, wherein movement of said handle relative to said blade from said working condition to at least one orientation between said working and folded conditions moves said jaws further apart.

17. The laryngoscope according to claim 16, wherein movement of said handle relative to said blade from said at least one orientation into said folded condition moves said jaws closer together.

18. The laryngoscope according to claim 15, wherein the jaws are configured to hold a proximal end of the blade within the jaws when the blade is at a fully extended working length, and wherein the proximal end of the blade extends outward from a rear portion of the jaws when a working length of the blade is less than a predetermined length.

19. A laryngoscope, comprising:
   a handle, wherein the handle has a coating of elastomeric and/or polymeric material;
   a blade configured to be inserted into a patient's mouth;
   a camera located within the blade;
   a light source located in the blade, wherein the light source is located remotely from the distal end of said blade;
   a light guide that directs light from said light source to a location adjacent to the distal end of the blade;
   a viewing device attached to the laryngoscope and configured to display an image;
   a plurality of electrical terminals provided on said blade and configured to connect said light source and camera to a power supply; and
   a mounting portion attached to the handle and the blade, the mounting portion allowing the blade to pivot with respect to the handle between a working position and a folded position, the mounting portion comprising a set of jaws that grip the blade, wherein movement of the blade from the working position to at least one orientation between the working and folded positions moves said jaws further apart so that a working length of the blade may be adjusted.

20. The laryngoscope according to claim 19, wherein the blade is securely gripped by the jaws of the mounting portion when the blade is in the folded and the working positions.

21. The laryngoscope according to claim 20, wherein movement of said blade from said at least one orientation into either the folded or working positions causes the jaws to move closer together.

22. The laryngoscope according to claim 19, wherein the mounting portion allows the blade to pivot through a plane that is offset from a central longitudinal axis of the handle in a direction perpendicular to the plane.

* * * * *